(12) United States Patent
Kanda (10) Patent No.: US 7,990,525 B2
(45) Date of Patent: Aug. 2, 2011

(54) FLOW CYTOMETER AND FLOW CYTOMETRY

(75) Inventor: Masahiko Kanda, Hyogo (JP)

(73) Assignee: Bay Bioscience Kabushiki Kaisha, Kobe-shi (JP)

( * ) Notice: Subject to any disclaimer, the term of this patent is extended or adjusted under 35 U.S.C. 154(b) by 304 days.

(21) Appl. No.: 11/988,386

(22) PCT Filed: Aug. 2, 2006

(86) PCT No.: PCT/JP2006/315290
§ 371 (c)(1),
(2), (4) Date: Jan. 7, 2008

(87) PCT Pub. No.: WO2007/018087
PCT Pub. Date: Feb. 15, 2007

(65) Prior Publication Data
US 2009/0122311 A1 May 14, 2009

(30) Foreign Application Priority Data
Aug. 8, 2005 (JP) .................. P2005-229536

(51) Int. Cl.
*G01N 21/00* (2006.01)
(52) U.S. Cl. .......................................... 356/73
(58) Field of Classification Search .............. 356/72–73, 356/318, 417; 250/458.1–461.1
See application file for complete search history.

(56) References Cited

U.S. PATENT DOCUMENTS

| | | | |
|---|---|---|---|
| 5,760,900 A * | 6/1998 | Ito et al. | 356/338 |
| 6,870,165 B2 * | 3/2005 | Amirkhanian et al. | 250/458.1 |
| 6,944,322 B2 * | 9/2005 | Johnson et al. | 382/128 |
| 2001/0026573 A1 * | 10/2001 | Takayama et al. | 372/46 |
| 2003/0058440 A1 | 3/2003 | Scott et al. | |

FOREIGN PATENT DOCUMENTS

| | | |
|---|---|---|
| EP | 1 432 966 | 6/2004 |
| JP | 61-173141 | 8/1986 |
| JP | 2003-315248 | 11/2003 |
| JP | 2005-524051 | 8/2005 |
| JP | 2006-275858 | 10/2006 |
| WO | WO 03/021212 | 3/2003 |

* cited by examiner

*Primary Examiner* — Tarifur Chowdhury
*Assistant Examiner* — Abdullahi Nur
(74) *Attorney, Agent, or Firm* — Harness, Dickey & Pierce, P.L.C.

(57) ABSTRACT

In one embodiment of the present invention, a flow cytometer includes a plurality of optical sources, each of which illuminates an excitation beam at a predetermined frequency having a wavelength and a phase different from another; and a guide member for guiding the excitation beams into the same incident optical path to focus onto a dyed particle. According to one aspect of an embodiment of the present invention, it is possible, without requiring introduction of the delay time, to detect a plurality of fluorescence excited at the cell particles labeled with a plurality of fluorescent labeling reagents, by a plurality of laser optical sources.

20 Claims, 8 Drawing Sheets

FLOW CYTOMETER AND FLOW CYTOMETRY

TECHNICAL FIELD OF INVENTION

The present invention relates to a flow cytometer and a flow cytometry.

DESCRIPTION OF RELATED ARTS

Recent rapid advances of biotechnology increases demands for a flow cytometer and a flow cytometry in various fields of technology such as medicine and biology, which automatically analyze and sort various type of biological cells. In general, the flow cytometer is adapted to arrange, in line within a sheath flow, each of cell particles that is sampled from biological body (e.g., blood) and then dyed with fluorescent labeling reagent. Also, it is designed to identify each of the cell particles by illuminating a laser beam thereon and detecting scattering beams (e.g., forward-scattered and side-scattered beams) and multicolor fluorescence emitted therefrom, of which colors depend upon the fluorescent labeling reagent. Thus, the flow cytometer may be used to make diagnosis on condition or disease of the biological body by transforming optical information of the scattered beams and the fluorescence into electrical information and by statistically evaluating electrical information for enormous amount of cell particles. Further, a cell sorter is adapted to use electrical information of each of the cell particles for selectively charging droplets containing desired cell particles, and apply direct electrical field horizontally along a passage through which the droplets fall, for collection of the particular cell particles.

Figure 7:
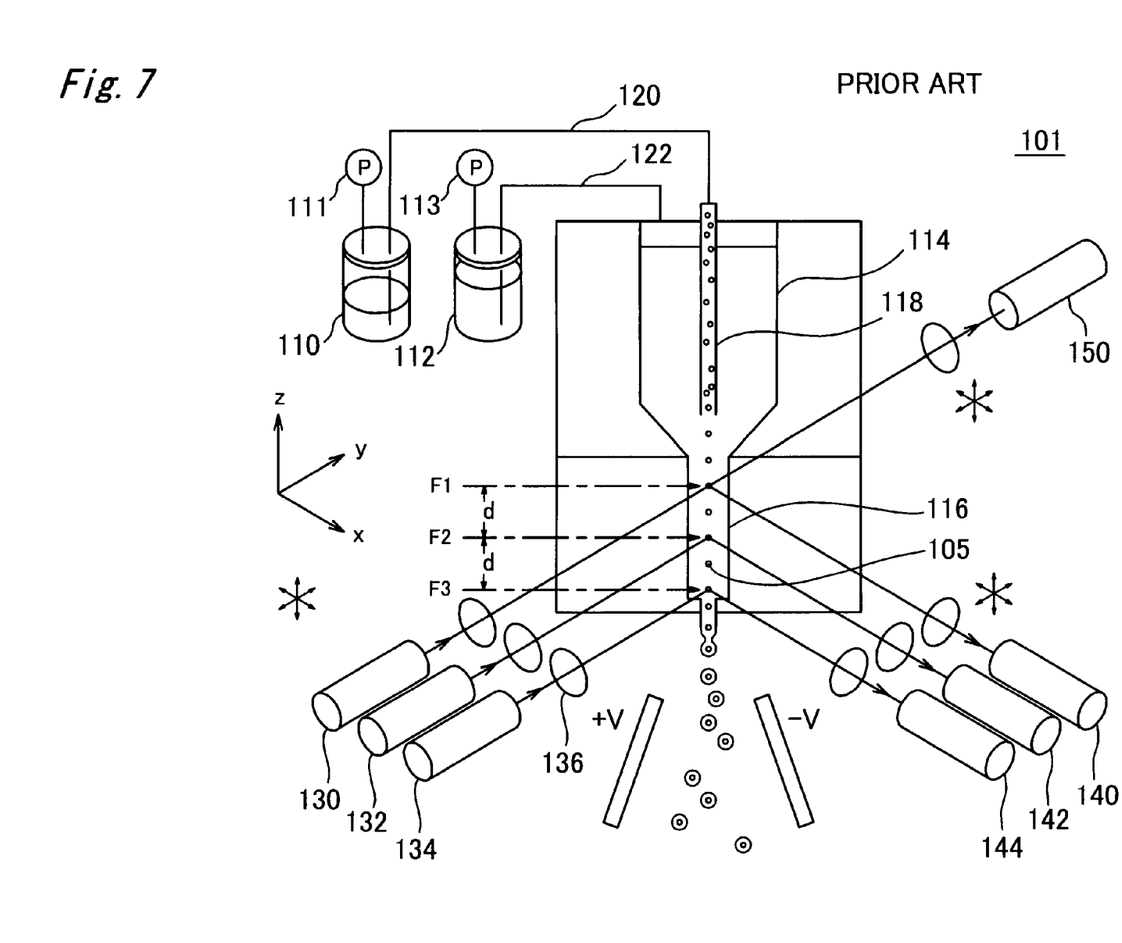
FIG. 7 schematically illustrates a structure of a conventional flow cytometer.
Figure 8:
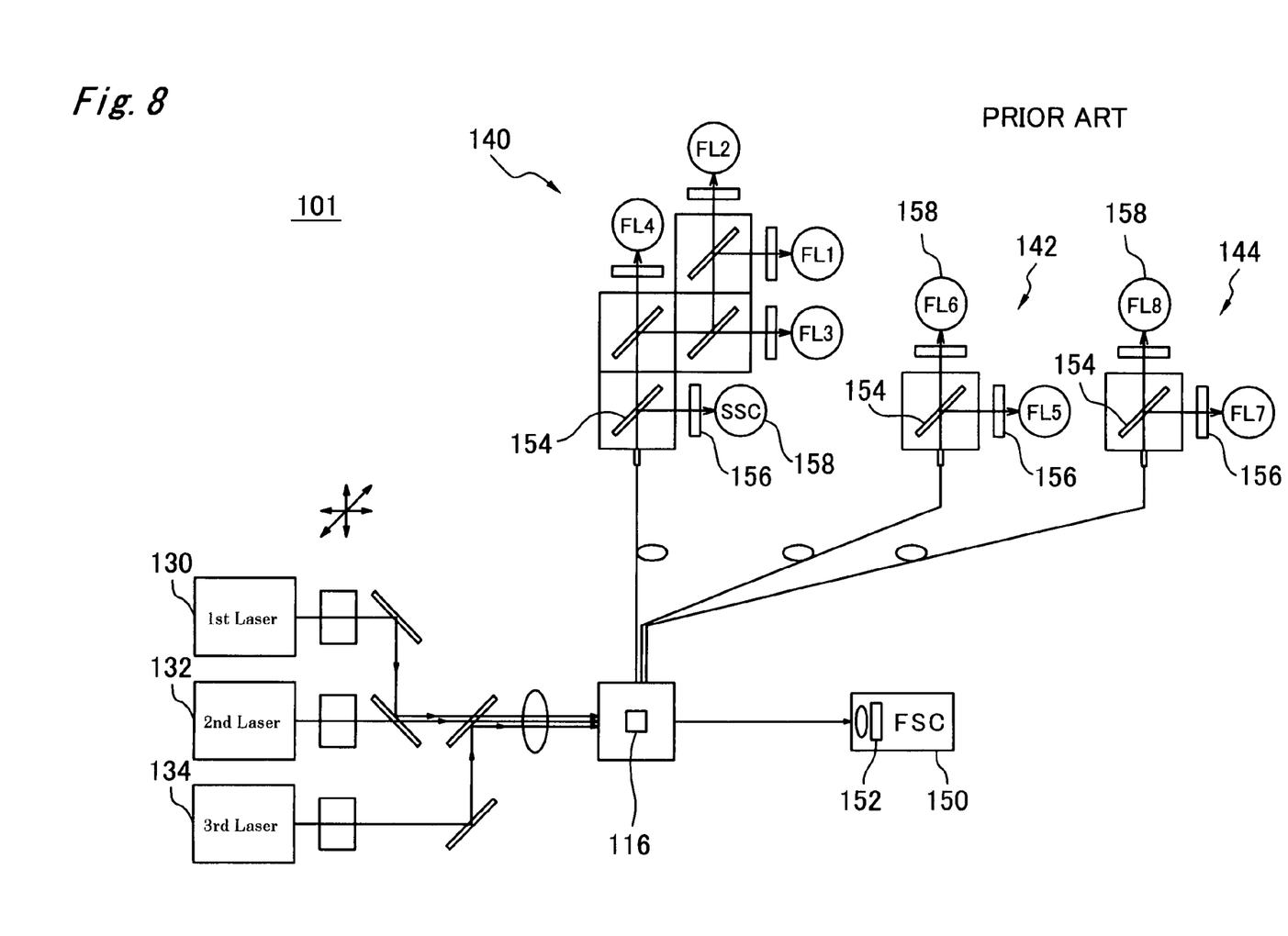
FIG. 8 is a block diagram of the flow cytometer illustrated in FIG. 7.

With reference to FIGS. 7 and 8, a conventional flow cytometer will be described in detail hereinafter. The conventional flow cytometer 101 illustrated in FIG. 7 comprises, in general, a fluid-dynamic mechanism for arranging each of cell particles dyed with fluorescent labeling reagent, in line within a sheath flow, and an optical mechanism for illuminating a plurality of laser beams of different wavelengths onto the cell particles and to detect scattered beams and fluorescence.

As illustrated in FIG. 7, the fluid-dynamic mechanism includes a sample suspension source 110 for storing and supplying sample suspension fluid, a sheath source 112 for storing and supplying sheath fluid, a flow chamber 114, and a flow cell 116 provided downward and connected to the flow chamber 114.

The flow chamber 114 is designed to have a substantially cylindrical form, and a suspension supply tube 118 is arranged along the center axis of the flow chamber. Air pumps 111, 113 apply pressure on the sample suspension fluid and sheath fluid in the sample suspension source 110 and the sheath source 112 which are supplied to the suspension supply tube 118 and the flow chamber 114 through a sample tube 120 and a sheath tube 122, respectively. This forms a sheath flow (laminar flow), in which the sheath fluid cylindrically encompasses the sample suspension fluid and each of the cell particles 105 in the sample suspension fluid is aligned one-by-one in the flow cell 116.

Meanwhile, the optical mechanism includes first, second and third optical sources 130, 132, 134, continuously illuminating laser beams (excitation beams) of different wavelengths. The first optical source 130 is a DPSS laser (Diode Pumped Solid State Laser) eliminating, e.g., a blue laser beam (peak wavelength: 488 nm, output: 20 mW). The second optical source 132 is a diode laser eliminating, e.g., a red laser beam (peak wavelength: 635 nm, output: 20 mW), and the third optical source 134 is a diode laser eliminating, e.g., a ultra-violet laser beam (peak wavelength: 375 nm, output: 8 mW).

The flow cytometer of the present invention is designed such that the laser beams of the first, second and third optical sources 130, 132, 134 are focused by light guide members such as collective lens 136 onto the flow cell 116 at different focal points F1, F2, F3, which are spaced by another with a predetermined gap d in a direction of the sheath flow (Z-direction).

As illustrated in FIG. 8, the optical mechanism includes a forward-scattering beam detecting apparatus 150 detecting FSC (Forward Scattering Light) that is scattered at cell particle by the first laser beam. Also, the optical mechanism has a first side-scattering-beam/fluorescence detecting apparatus 140 detecting SSC (Side Scattering Light) that are scattered at the cell particle 105 by each of the blue, red, ultraviolet beams, and also detecting fluorescence of various wavelengths that are excited at the cell particle 105 by the blue laser beam. Further, the optical mechanism includes second and third fluorescence detecting apparatuses 142, 144 detecting fluorescence of various wavelengths that are excited at the cell particle 105 by the red and ultra-violet laser beams, respectively.

As shown in FIG. 8, the forward-scattering beam detecting apparatus 150 includes a photodetector 152 detecting FSC of the first laser beam 130. Also, the first side-scattering-beam/fluorescence detecting apparatus 140 includes a plurality of half-mirrors 154, band-pass-filters 156, and photomultiplier tubes 158. Each of the second and third fluorescence detecting apparatuses 142, 144 includes a half-mirror 154, two band-pass-filters 156, and a photomultiplier tube 158. According to the conventional technology, the first side-scattering-beam/fluorescence detecting apparatus 140 detects SSC and fluorescence caused by the first optical source (blue laser) 130, and the second and third fluorescence detecting apparatuses 142, 144 detect fluorescence excited by the second and third optical sources (red and ultra-violet beams), respectively. As above, the conventional flow cytometer focuses a plurality of continuously oscillating laser beams on different focal points spaced by another with a gap d, and independently detects the scattering beams and the fluorescence at each of the focal points, thereby outputting signals therefor to a signal processor (not shown).

The signal processor is adapted to process analog signals output from the forward-scattering beam detecting apparatus 150, the first side-scattering-beam/fluorescence detecting apparatus 140, and the second and third fluorescence detecting apparatuses 142, 144. As above, while the first, second and third laser beams are continuously emitted on the different focal points spaced by another with the gap d, the signal processor calculates a first delay time after receiving the fluorescence excited by the first laser beam before receiving the fluorescence excited by the third laser beam, and also a second delay time after receiving the fluorescence excited by the second laser beam before receiving the fluorescence excited by the third laser beam. Then, the signal processor tentatively stores signals regarding the fluorescence excited by the first and second laser beams in a FIFO memory for the first and second delay times, respectively, thereby to output a plurality of signals with regard to the same cell particle at the same time. Thus, the signal processor processes several scattering beams and fluorescence from the single cell particle 105 for identification thereof.

International Patent Application, WO 2004/051238, discloses a flow cytometer, of which basic structure is similarly designed to aforementioned conventional flow cytometer, although it has two optical sources rather three, which is entirely incorporated herein by reference into the present application.

DISCLOSURE OF INVENTION

Problems to be Solved by Invention

In the meanwhile, the aforementioned delay times may be susceptive and varied with flow rate of the sheath flow (depending upon, e.g., pressure of the air pumps for the sample suspension fluid and the sheath fluid). Therefore, since the operator often has a difficulty to properly control and maintain the flow rate of the sheath flow, which may reduce efficiency and accuracy in sorting the cell particle.

Also, the conventional structure requires a plurality of light guide members for guiding beams from the optical sources onto the flow cell at the different focal points, which brings burdensome task with adjustment of light axes.

The present invention address those above-described drawbacks, and one of aspects of the present invention is to provide a flow cytometer and a flow cytometry, which enables detection of several fluorescence excited by multiple laser sources at the cell particle labeled with fluorescent dyes for identification of the cell particle, without using the delay times.

Also, another aspect of the present invention is to provide a flow cytometer and a flow cytometry, which simplifies the optical axes to the cell particle running through the sheath flow.

Means for Solving Problems

According to one of aspects of the present invention, a flow cytometer is provided, which comprises a plurality of optical sources, each of which illuminates an excitation beam at a predetermined frequency having a wavelength and a phase different from another; and a guide member for guiding the excitation beams into the same incident optical path to focus onto a dyed particle.

According to another one of aspects of the present invention, a flow cytometry is provided, which comprises illuminating a plurality of excitation beams at a predetermined frequency having a wavelength and a phase different from another; and guiding the excitation beams into the same incident optical path to focus onto a dyed particle.

Preferably, the particle flows within a sheath flow intersecting with the incident optical path.

Also the flow cytometer further comprises a plurality of fluorescent detectors for detecting fluorescence from the particle excited by each of the excitation beams to output fluorescent signals; and a synchronizing/isolating circuitry for isolating the fluorescent signals in synchronization with each of the phases of the excitation beams into a plurality of optical signal components.

Preferably, the fluorescent detector includes a photomultiplier tube, of which photo-multiplying voltage is selectively switched in accordance with respective one of the phases of the excitation beams.

Alternatively, an amplifying circuitry is provided for electrically amplifying the fluorescent signals, of which amplifying voltage is selectively switched in accordance with respective one of the phases of the excitation beams.

Preferably, a plurality of band pass filters are provided in outgoing optical paths between the flow cell and the fluorescent detectors, for selectively transmitting fluorescence having predetermined spectrums.

Also, the flow cytometer further comprises a forward-scattering beam detector for detecting a forward scattering beam scattered at the particle by each of the excitation beams, to output forward-scattering signals, wherein each of the fluorescent detectors detects the fluorescence for predetermined time duration after the forward-scattering signals exceed a predetermined threshold.

Alternatively, the flow cytometer further comprises a forward-scattering beam detector for detecting a forward scattering beam scattered at the particle by each of the excitation beams, to output forward-scattering signals, wherein the fluorescent detectors include at least one trigger fluorescent detector, and wherein the forward-scattering beam detector and each of the fluorescent detectors detect the forward scattering beam and the fluorescence for predetermined time duration after the fluorescent signals detected by the trigger fluorescent detector exceed a predetermined threshold.

Furthermore, the flow cytometer comprises a forward-scattering beam detector for detecting a forward scattering beam scattered at the particle by each of the excitation beams, to output forward-scattering signals; a forward-scattering beam band pass filter provided in outgoing optical path between the flow cell and the forward-scattering beam detector, for selectively transmitting the forward scattering beam having predetermined spectrums; a side-scattering-beam detector for detecting a side scattering beam scattered at the particle by each of the excitation beams, to output side-scattering signals; and a side-scattering-beam band pass filter provided in outgoing optical path between the flow cell and the side-scattering-beam detector, for selectively transmitting the side scattering beam having predetermined spectrums.

Preferably, the optical sources oscillate the excitation beams in a pulsed form at a predetermined frequency having the phase different from another.

Advantage of Invention

According to one aspect of the flow cytometer and the flow cytometry of the present invention, it is possible, without requiring introduction of the delay time, to detect a plurality of fluorescence excited at the cell particles labeled with a plurality of fluorescent labeling reagents, by a plurality of laser optical sources.

Also, another aspect of the present invention is to provide a flow cytometer and a flow cytometry, it is possible to substantially simplify adjusting the optical axes.

BRIEF DESCRIPTION OF REFERENCE NUMERALS

1: flow cytometer, 2: fluid-dynamic mechanism, 3: optical mechanism, 4: signal processor, 5: cell particle, 10: sample suspension source, 11, 13: air pump, 12: sheath source, 14: flow chamber, 16: flow cell, 18: suspension supply tube, 20: sample tube, 22: sheath tube, 24: orifice, 26: droplet, 28a, 28b: deflecting plate, 30, 32, 34: optical source, 36: guiding member, 37: fiber optics, 38: beam expander, 39: half-mirror, 40: collective lens, 42: forward-scattering beam detecting apparatus, 50: side-scattering-beam/fluorescence detecting apparatus, 52: fiber optics, 54: collimating rod lens, 62: clock-pulse generating circuitry, 64: laser driving circuitry, 66: synchronizing circuitry, 68: isolating circuitry, 70: amplifying circuitry, 72: analog-digital converting circuitry, 74: area/width/height calculating circuitry, 76: parameter-selecting circuitry, 78: compensating circuitry, 80: log/linear amplifying circuitry, 82: computer, 84: cell sorter, PD: photodetector, PMT1-PMT6: photomultiplier tube, HM1-HM6: half mirror, BP1-BP6: band pass filter.

BEST MODE FOR CARRYING OUT INVENTION

With reference to attached drawings, a flow cytometer and a flow cytometry according to the present invention will be described herein. In this description, although the terminology indicating the directions (for example, "X-", "Y-" and "Z-directions") is conveniently used just for clarity, it should not be interpreted that those terminology limit the scope of the present invention.

Figure 1:
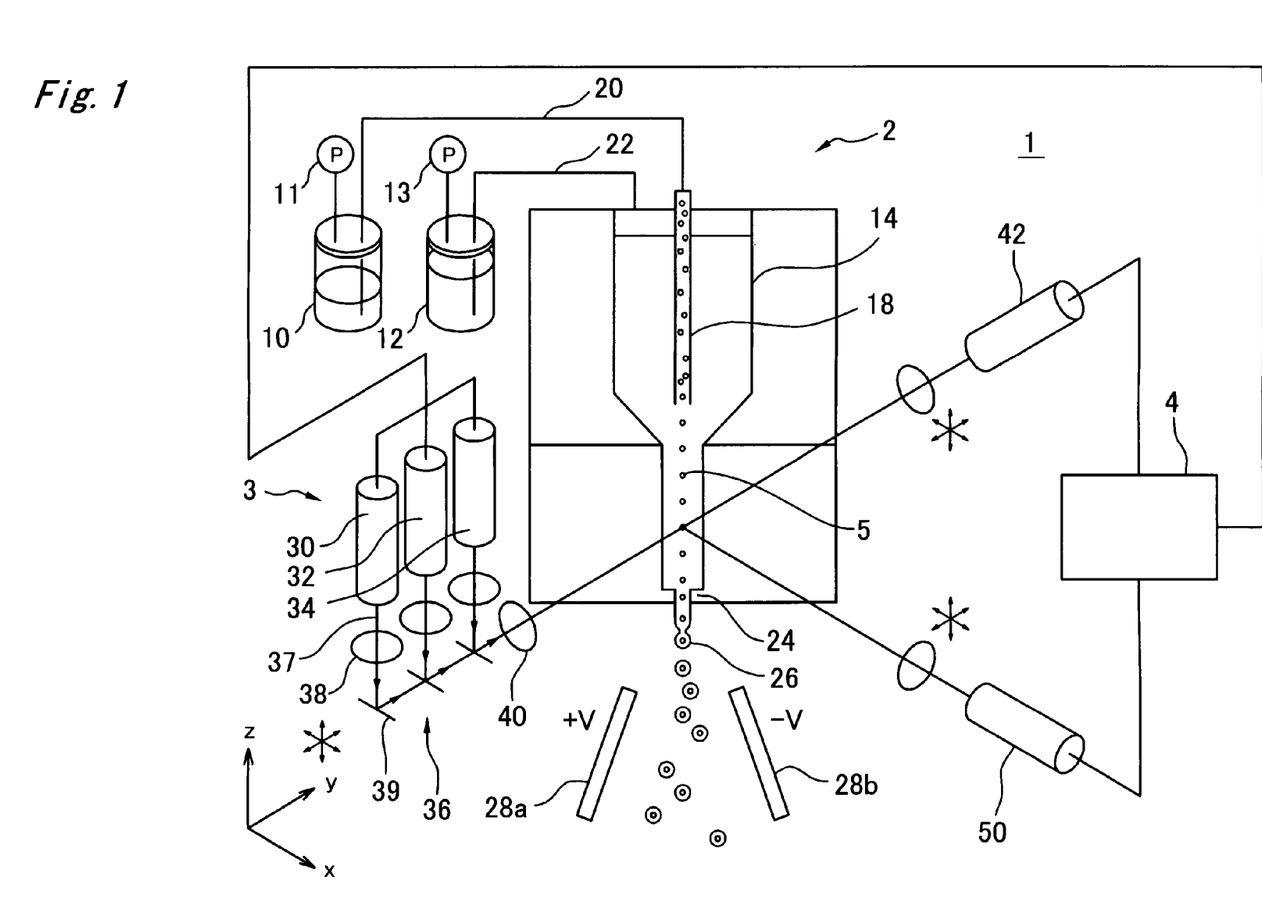
FIG. 1 schematically illustrates a structure of the flow cytometer according to the present invention.

Referring to FIGS. 1-6, embodiments of the flow cytometer and the flow cytometry according to the present invention will be described herein. As illustrated in FIG. 1, the flow cytometer 1 of the present invention includes, in general, a fluid-dynamic mechanism 2 for arranging each of cell particles dyed with fluorescent labeling reagent, in line within a sheath flow. Also, it includes an optical mechanism 3 for illuminating a plurality of laser beams of different wavelengths onto the cell particles and for detecting scattered beams and fluorescence. Further, it includes a signal processor 4 for controlling and processing electrical signals regarding the scattering beams and the fluorescence output by the optical mechanism 3.

Firstly, the fluid-dynamic mechanism 2 will be described herein. As illustrated in FIG. 1, the fluid-dynamic mechanism 2 includes a sample suspension source 10 for storing and supplying sample suspension fluid, a sheath source 12 for storing and supplying sheath fluid, a flow chamber 14, and a flow cell 16 provided downward and connected to the flow chamber 14. The cell particles to be analyzed are labeled with fluorescent labeling reagent such as fluorescent dye and fluorescent monoclonal antibody. It should be noted that although the flow cytometer incorporating a flow cell is discussed in this application, the present invention can equally be applied to a jet-in-air type flow cytometer.

Although not limited thereto, the fluorescent labeling reagents are commonly known in the art, including, for instance, FITC (Fluorescein) emitting greenish-yellow fluorescence excited by blue excitation beam, PE (R-phycoerythrin) emitting greenish-yellow fluorescence excited by blue excitation beam and its tandem fluorescent labeling reagent such as PE-Cy5 (red fluorescence) or PE-Cy7 (infrared fluorescence), APC (Allophycocyanin) emitting red fluorescence excited by orange excitation beam and its tandem fluorescent labeling reagent such as APC-Cy5 (infrared fluorescence), and HO(Hoechest 33342)-Blue (blue fluorescence) and HO-Red (red fluorescence) emitting fluorescence excited by ultra-violet excitation beam.

The flow chamber 14 is designed to have a substantially cylindrical form, and a suspension supply tube 18 is positioned along the center axis of the flow chamber. Air pumps 11, 13 apply pressure on the sample suspension fluid and sheath fluid in the sample suspension source 10 and the sheath source 12 which are supplied to the suspension supply tube 18 and the flow chamber 14 through a sample tube 20 and a sheath tube 22, respectively. This forms a sheath flow (laminar flow), in which the sheath fluid cylindrically encompasses the sample suspension fluid. The pressure on the sample suspension fluid is adjusted to be slightly less than the pressure on the sheath fluid so that the sample suspension fluid encompassed by the sheath fluid has reduced (thin) cross sectional area (fluid-dynamic constriction) thereby to align each of the cell particles 5 one-by-one in the flow cell 16 spaced by another with a substantially equal gap.

The flow cell 16 has an orifice 24 at the bottom so that the sheath flow with the cell particle 5 is jet (rapidly ejected) through the orifice 24. An oscillator such as a piezoelectric element (not shown) is provided for applying oscillation with the ejected sheath flow to form droplets 26 containing the cell particles 5.

In order to sort the droplets 26 containing desired cell particles (i.e., when used as a cell sorter), an electron charger (not shown) is provided for charging the sheath flow containing the desired cell particles 5 just before a break-off point where the droplet 26 is being separated from the sheath flow. Also, provided is a pair of deflecting plates 28a, 28b, across which a predetermined voltage (e.g., a direct voltage of 6000V) is applied, to generate direct electrical field so that the charged droplets 26 are forced by the electrical field to be deflected and sorted when falling between the deflecting plates 28a, 28b.

Next, the optical mechanism 3 will be described herein. The optical mechanism 3 illustrated in FIG. 1 includes first, second and third optical sources 30, 32, 34, illuminating laser beams (excitation beams) of different wavelengths onto each of the cell particles aligned within the flow cell 16. The first, second and third optical sources 30, 32, 34 may be any types of optical sources and not limited thereto, preferably, they emit coherent beams such as laser beams. As an example, the first optical source 30 may be a DPSS laser (Diode Pumped Solid State Laser) eliminating a blue laser beam (peak wavelength: 488 nm, output: 20 mW). The second optical source 32 may be a diode laser eliminating a red laser beam (peak wavelength: 635 nm, output: 20 mW), and the third optical source 34 may be a diode laser eliminating a ultra-violet laser beam (peak wavelength: 375 nm, output: 8 mW).

Figure 2A:
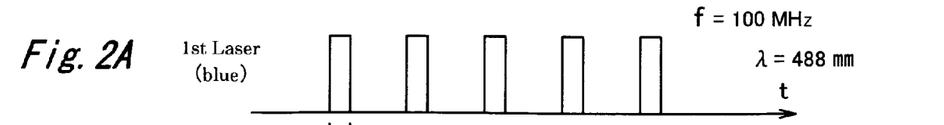
FIGS. 2A-2I are timing charts of the pulsed beams generated by the optical sources of FIG. 1 and the pulsed beam signals output by the photomultiplier tubes.
Figure 2B:
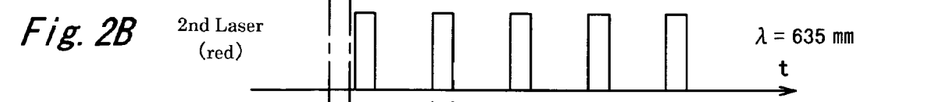
Figure 2C:
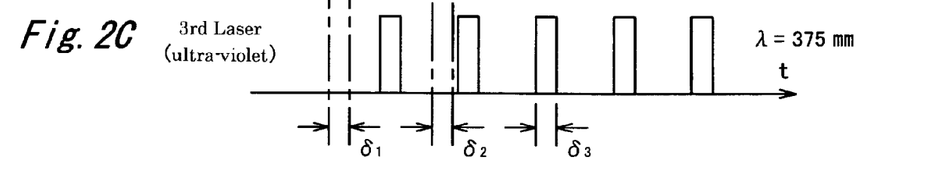

According to the present embodiment, a modulator (not shown) is built in each of the optical sources 30, 32, 34 for pulse oscillation (pulsed modulation) of the laser beams in accordance with a clock pulse signal generated by a clock pulse generating circuitry 63 (see FIG. 5) as will be described, for example, at a predetermined oscillation frequency (e.g., f=100 MHz). As illustrated in FIGS. 2A-2C, each of the laser beams output from respective one of the optical sources 30, 32, 34 is modulated so as to have the pulse wave which is not coincident with another (without overlapping). Thus, the first, second and third optical sources 30, 32, 34 of this embodiment are adapted to generate the pulsed laser beams (excitation beams), having the same frequency but different first, second and third phases $\delta_1$, $\delta_2$, $\delta_3$. When the oscillation frequency is set to be 100 MHz or more, for example, the pulse width of each of the laser beams is 0.01 µs or less.

Any types of the modulators integrated in the optical source may be used, including, for example, an acoustic-optical modulator (Model No. TEM-85-10) for the DPSS laser 30, which is commercially available from Brimrose Corporation (Baltimore, Md., USA), and a universal semiconductor modulator for the red and ultra-violet diode lasers, for pulse modulation. Also, a mode-locked laser may be used to pulse the laser beam as well as to substantially intensify the peak of the laser beam, thereby improving detection sensitivity.

Figure 3:
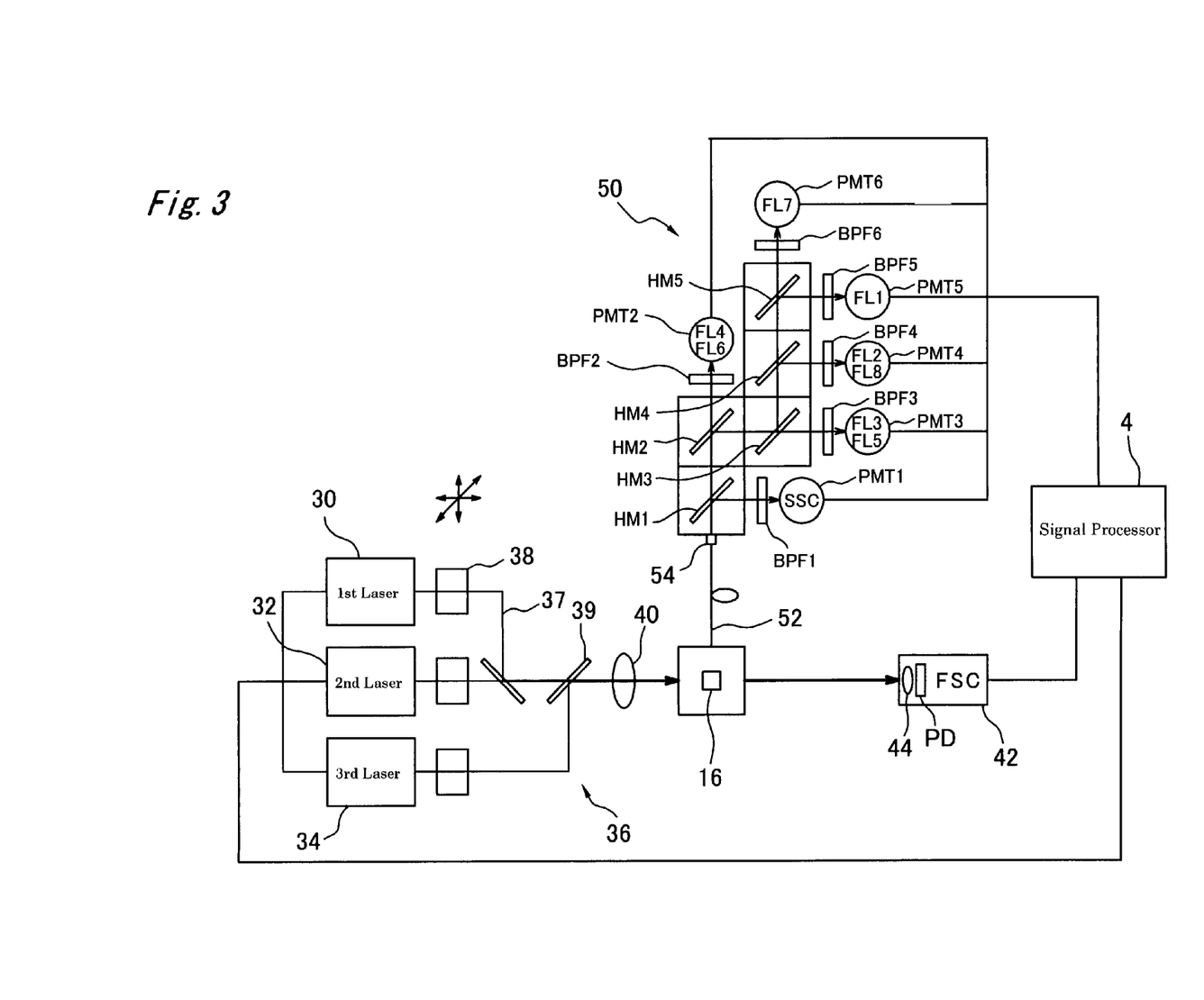
FIG. 3 is a block diagram of the flow cytometer illustrated in FIG. 1.

The pulsed laser beams output from the first, second and third optical sources 30, 32, 34 are guided to the same optical path by means of guiding members 36 for illumination onto the same point of the flow cell 16, as illustrated in FIGS. 1 and 3. The guiding members 36 may include, for example, fiber optics 37, beam expanders 38, half-mirrors 39, and collective lens 40, of which position may be shifted partially or entirely in X-, Y-, or Z-direction so that those laser beams output from the first, second and third optical sources are aligned in the same optical path.

Also, as shown in FIGS. 1 and 3, the optical mechanism 3 of the preferred embodiment includes a forward-scattering beam detecting apparatus 42 for detecting FSC (Forward Scattering Light) that is scattered at cell particle 5 by the blue laser beam, and a side-scattering-beam/fluorescence detecting apparatus 50 for detecting SSC (Side Scattering Light) that are scattered at the cell particles 5 by each of the blue, red, ultraviolet beams, and also for detecting fluorescence of various wavelengths that are excited at the cell particles 5 by those laser beams. The forward-scattering beam detecting apparatus 42 includes a band pass filter (not shown) for selectively transmitting the blue laser beam (for example, selective spectrum for transmission is 488±5 nm) thereby to detect the FSC scattered at cell particle 5 by the blue laser beam. Also, the side-scattering-beam/fluorescence detecting apparatus 50 is adapted to detect the SSC of wavelengths same as those of the laser beams and the fluorescence of various wavelengths different from those of the laser beams.

Referring to FIGS. 2-6, the details of the forward-scattering beam detecting apparatus 42, the side-scattering-beam/fluorescence detecting apparatus 50, and the signal processor will be described herein.

The forward-scattering beam detecting apparatus 42 includes a photodetector PD (see FIG. 3) for detecting the forward scattering beam transmitted from flow cell 16 through the collective lens 44, and the above-mentioned band pass filter for selectively transmitting only the blue laser beam scattered at cell particle 5 by the blue laser beam. Then the forward-scattering beam detecting apparatus 42 outputs electrical signals to the signal processor 4, of which amplitude varies in accordance with strength of the blue pulsed FSC.

Figure 4:
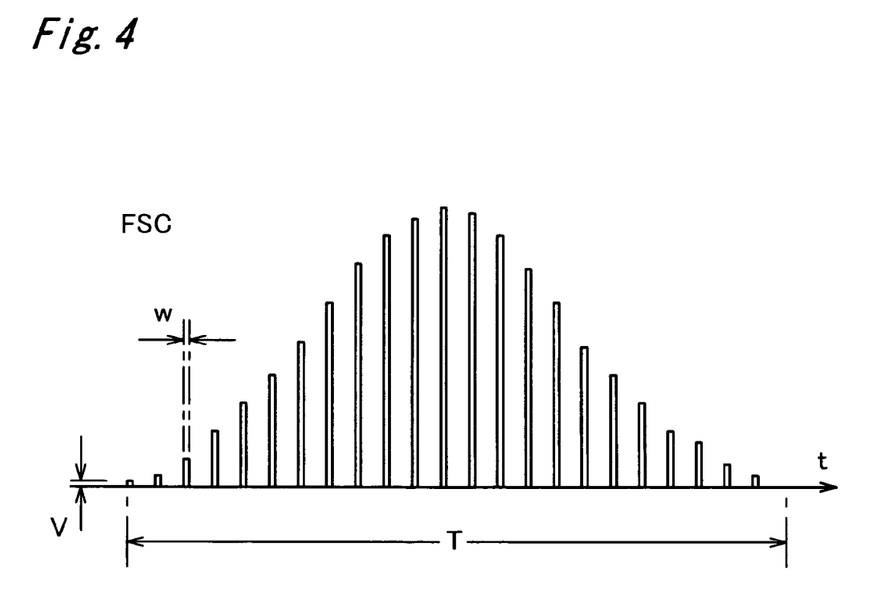
FIG. 4 is a timing chart of the pulsed beam signal output by the optical source of FIG. 3, for the forward scattering beam.

Since the photodetector PD detects the forward scattering beam scattered at a single cell particle 5 running through the flow cell 16 along the Z-direction, the electrical signals of the forward scattering beam has the amplitude varying in time as shown in FIG. 4. Therefore, time duration T, for which the forward scattering beam is detected or a single cell particle 5 is illuminated, depends upon a size of the cell particle 5 running through the flow cell 5 and flow rate of the sheath flow (i.e., pressure of the air pump 11). For instance, where the pressure of the air pump 11 is about 30 psi and the cross section area of the flow cell is about 20000 µm², it is known that the time duration T would be about 100 µs. Therefore, when the laser beams from the optical sources 30, 32, 34 are pulse-modulated at an oscillation frequency of 100 MHz without substantial intermission, a width w of one pulsed laser beam is 0.01 µs. Thus, during the time duration T, about one thousand of pulsed laser beams are output alternately by three of the optical sources so that about 333 of pulsed blue laser beams are detected. In FIG. 4, the width w of the pulsed laser beam is illustrated to be greater for clarity of the drawing.

In other words, it is determined that the cell particle 5 is crossing the focal point in the flow cell 16 upon detection of the forward-scattering pulsed signals, or for example, upon detection of the amplitude V of the forward-scattering pulsed signals that exceed a threshold voltage $V_{th}$ ($V > V_{th}$). Therefore, as will be described herein in detail, the signal processor 4 initiate to retrieve data as the FSC pulsed signals, the SSC pulsed signals, and the pulsed fluorescence signals, for a predetermined time duration T after the amplitude V of the forward-scattering pulsed signals is determined to be greater than the threshold voltage $V_{th}$.

Next, the details of the side-scattering beam/fluorescence detecting apparatus 50 will be described herein. In FIG. 3, after the blue, red, ultra-violet laser beams are illuminated onto the cell particles 5 that are aligned in line within the flow cell 16, the side scattering beam and the fluorescence of different spectrums are received by the side-scattering beam/fluorescence detecting apparatus 50 through the fiber optics 52 and the collimating rod lens 54.

In the present embodiment, the first, second and third optical sources 30, 32, 34 illuminate a blue laser beam (peak wavelength: 488 nm), a red laser beam (peak wavelength: 635 nm), and a ultra-violet laser beam (peak wavelength: 375 nm), respectively. Also, the cell particles 5 are labeled with the fluorescent labeling reagent including FITC, PE, PE-Cy5, PE-Cy7, APC, APC-Cy5, HO-Blue, and HO-Red.

The side-scattering beam/fluorescence detecting apparatus 50 includes, in general, photomultiplier tubes PMT1-PMT6 for electrically amplifying and detecting faint light, half mirrors HM1-HM6, and band pass filters BP1-BP6 for selectively transmitting light of only a predetermined spectrum.

Figure 2D:
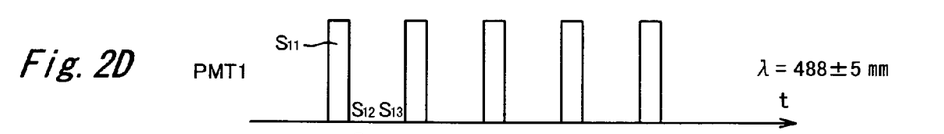

The side scattering beams and fluorescence through the rod lens 54 incident onto the half mirror HM1 and a portion thereof reflects to the band pass filter BP1. The band pass filter BP1 is designed to selectively transmit the side scattering blue beam only, of which wavelength is the same as that of the first optical source 30 (488±5 nm). Thus, the photomultiplier tube PMT1 detects the pulsed signal for the side scattering beam, as illustrated in FIG. 2D.

In general, the other portions of light through the half mirror HM1 are reflected at and/or transmitted through the half mirror HM2-HM6 to the photomultiplier tubes PMT2-PMT6. Thus, each of the photomultiplier tubes PMT2-PMT6 detects multiple of fluorescence having different wavelengths in the oscillation frequency and at the phases of the blue, red, and ultra-violet laser beams. In order to identify the cell particle 5, since it is preferable for each of the photomultiplier tubes PMT2-PMT6 to detect the fluorescence having possibly many different wavelengths, the side-scattering beam/fluorescence detecting apparatus 50 is structured so as to selectively detect the fluorescence having particular spectrums by means of the half mirrors HM2-HM6 and the band pass filters BPF2-BPF6, of which spectrums are optionally selected.

Figure 2E:
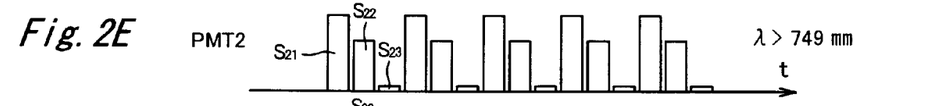

In an exemplary side-scattering-beam/fluorescence detecting apparatus 50 shown in FIG. 3, light through the half mirror HM1 is illuminated on the half mirror HM2 which reflects light having wavelength less than 730 nm and transmits light having wavelength of 730 nm or more. Light through the half mirror HM2 is illuminated on the band pass filter BPF2 which transmits light having wavelength greater than 749 nm. Therefore, the photomultiplier tube PMT2 detects the fluorescence having wavelengths greater than 749 nm, at the first, second and third phases $\delta_1$, $\delta_2$, $\delta_3$ which correspond to those of the first, second and third laser beams, as illustrated in FIG. 2E. In the present application, a set of optical signal components of the optical pulsed signals detected by the photomultiplier tube PMT2 at the phases $\delta_1$, $\delta_2$, $\delta_3$ are defined herein as $S_{21}$, $S_{22, 23}$, respectively. Thus, the optical signal components $S_{21}$, $S_{22, 23}$ correspond to fluorescence having wavelength greater than 749 nm, which are excited by the optical sources 30-34, respectively, and the photomultiplier tube PMT2 detects a set of optical pulsed signals consisting of the optical signal components $S_{21}$, $S_{22}$, $S_{23}$.

Figure 2F:
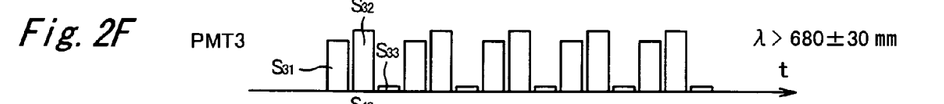

Back to FIG. 3, light reflecting at the half mirror HM2 is illuminated on the half mirror HM3 which reflects light having wavelength less than 600 nm and transmits light having wavelength of 600 nm or more. Light through the half mirror HM3 is selected by the band pass filter BPF3 which transmits light having wavelength of 680±30 nm. Thus, the photomultiplier tube PMT3 detects the fluorescence having wavelengths of 680±30 nm at the first, second and third phases $\delta_1$, $\delta_2$, $\delta_3$, as illustrated in FIG. 2F, and outputs optical signal components $S_{31}$, $S_{32, 33}$. Similarly, the optical signal components $S_{31}$, $S_{32}$, $S_{33}$ correspond to fluorescence having wavelength of 680±30 nm, which are excited by the optical sources 30-34, respectively.

Figure 2G:
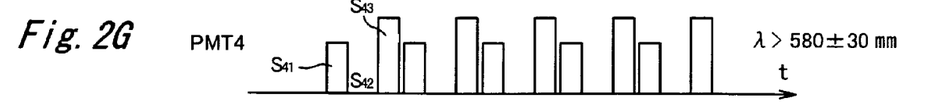

Then, light reflecting at the half mirror HM3 is illuminated on the half mirror HM4 which transmits light having wavelength less than 550 nm and reflects light having wavelength of 550 nm or more. Light reflecting at the half mirror HM4 is divided by the band pass filter BPF4 which transmits light having wavelength of 580±30 nm. Thus, the photomultiplier tube PMT4 detects the fluorescence having wavelengths of 580±30 nm at the first, second and third phases $\delta_1$, $\delta_2$, $\delta_3$, as illustrated in FIG. 2G, and outputs optical signal components $S_{41}$, $S_{42}$, $S_{43}$. In this context, while the excitation beam of the red laser beam cannot excite fluorescence having shorter wavelength of 580±30 nm, the optical signal component $S_{42}$ indicates the self-fluorescence which is not based upon the fluorescence reagent.

Figure 2H:
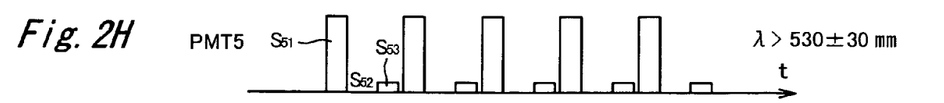

Then, light through the half mirror HM4 is illuminated on the half mirror HM5 which transmits light having wavelength less than 505 nm and reflects light having wavelength of 505 nm or more. Light reflecting at the half mirror HM5 is divided by the band pass filter BPF5 which transmits light having wavelength of 530±30 nm. Thus, the photomultiplier tube PMT5 detects the fluorescence having wavelengths of 530±30 nm at the first, second and third phases $\delta_1$, $\delta_2$, $\delta_3$, as illustrated in FIG. 2H, and outputs optical signal components $S_{51}$, $S_{52}$, $S_{53}$. Similar to the photomultiplier tube PMT4, since the excitation beam of the red laser beam cannot excite fluorescence having wavelength shorter than that of the excitation beam, the optical signal component $S_{52}$ indicates the self-fluorescence which is not based upon the fluorescence reagent.

Figure 2I:
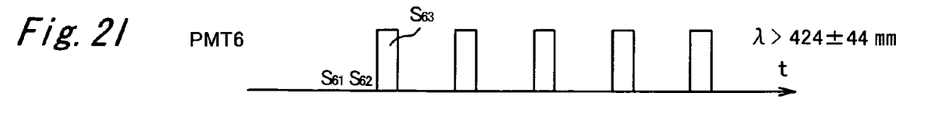

Light through the half mirror HM5 is divided by the band pass filter BPF6 which transmits light having wavelength of 424±44 nm. Thus, the photomultiplier tube PMT5 detects the fluorescence having wavelengths of 424±44 nm at the first, second and third phases $\delta_1$, $\delta_2$, $\delta_3$, as illustrated in FIG. 2I, and outputs optical signal components $S_{61}$, $S_{62}$, $S_{63}$. Similar to the photomultiplier tubes PMT4, PMT5, since the excitation beam of the red and blue laser beams cannot excite fluorescence having wavelength shorter than those of the excitation beam, the optical signal components $S_{61}$, $S_{62}$ indicate the self-fluorescence which are not based upon the fluorescence reagent.

Figure 5:
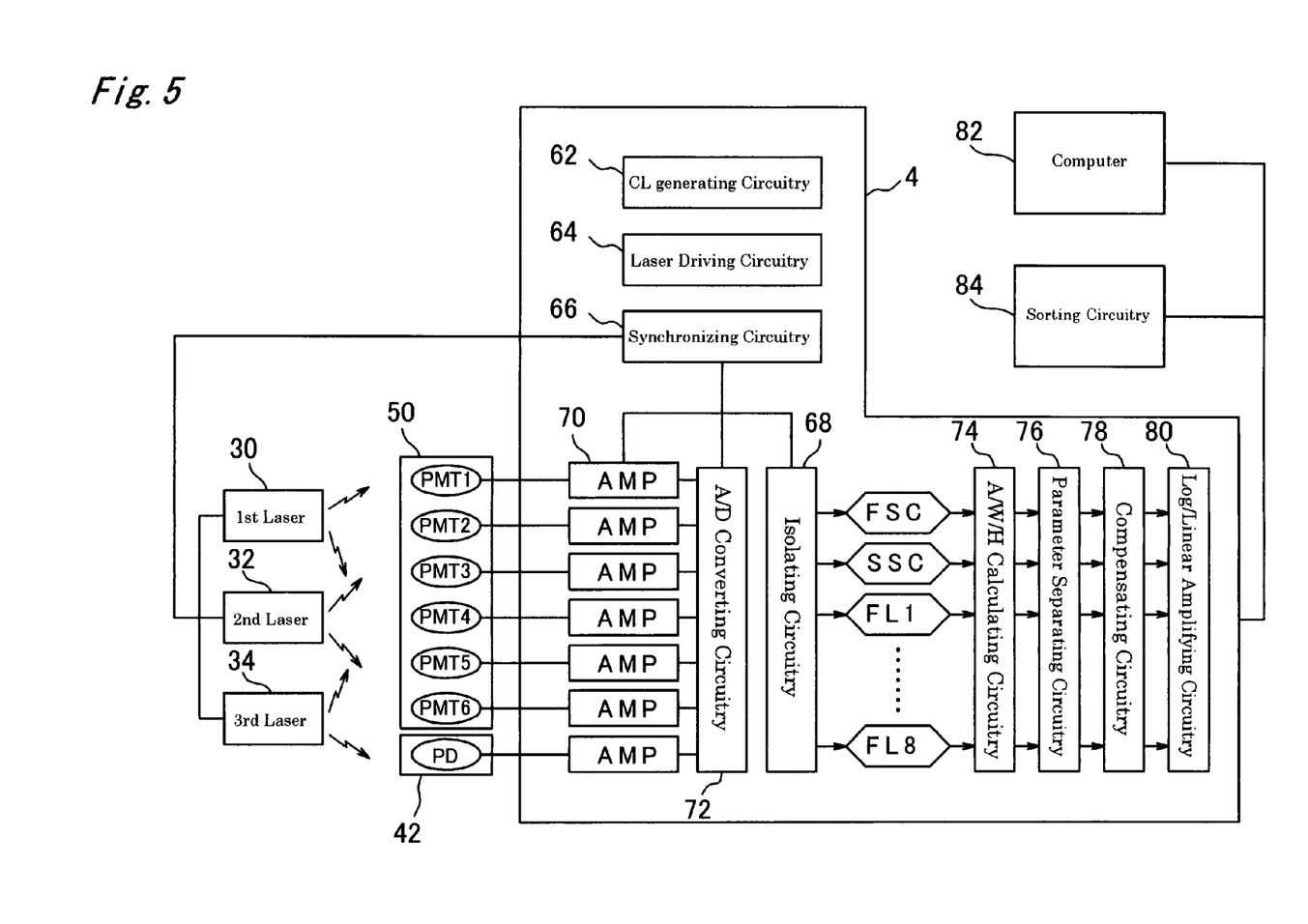
FIG. 5 is a block diagram of a digital signal processor illustrated in FIG. 3.

Meanwhile, as illustrated in FIG. 5, the signal processor 4 includes a clock-pulse generating circuitry 62 and a laser driving circuitry 64 connected thereto, which drives the first, second and third optical sources 30-34 for pulsed oscillation of the same frequency at different phases ($\delta_1$, $\delta_2$, $\delta_3$) as described above. Also, the signal processor 4 includes a synchronizing circuitry 66 which is electrically connected with the laser driving circuitry 64, the photomultiplier tubes PMT1-PMT6, an amplifying circuitry (AMP) 70, and an isolating circuitry 68.

The synchronizing circuitry 66 of the signal processor 4 is adapted to synchronize the optical pulsed signals output from the photodetectors PD and the photomultiplier tubes PMT1-PMT6 with the first, second and third phases $\delta_1$, $\delta_2$, $\delta_3$. Then, the isolating circuitry 68 of the signal processor 4 is adapted to isolate each of the optical pulsed signals output from the photomultiplier tubes PMT1-PMT6 into the optical signal components S as follows.

TABLE 1

|  | First Laser | Second Laser | Third Laser |
|---|---|---|---|
| PMT1<br>$\lambda = 488 \pm 5$ nm | $S_{11}$(SSC) | $S_{12}$ | $S_{13}$ |
| PMT2<br>$\lambda > 749$ nm | $S_{21}$(FL4) | $S_{22}$(FL6) | $S_{23}$ |
| PMT3<br>$\lambda = 680 \pm 30$ nm | $S_{31}$(FL3) | $S_{32}$(FL5) | $S_{33}$ |
| PMT4<br>$\lambda = 580 \pm 30$ nm | $S_{41}$(FL2) | $S_{42}$ | $S_{43}$(FL8) |
| PMT5<br>$\lambda = 530 \pm 30$ nm | $S_{51}$(FL1) | $S_{52}$ | $S_{53}$ |
| PMT6<br>$\lambda = 424 \pm 44$ nm | $S_{61}$ | $S_{62}$ | $S_{63}$(FL7) |

The optical signal component $S_{11}$ is output by detecting light having wavelength ($\lambda$=488±5 nm) same as that of the first laser beam 30, thus it represents the side scattering light (SSC). Also, the optical signal component $S_{21}$ is output by detecting infrared fluorescence ($\lambda$>749 nm) after excitation of the blue laser beam, which corresponds to infrared fluorescence (FL4) emitted from the cell particle dyed with the fluorescent labeling reagent of PE-Cy7. Also, the optical signal component $S_{22}$ represents amplitude of infrared fluorescence (FL6) emitted from the cell particle dyed with the fluorescent labeling reagent of APC-Cy7 after excitation of the red laser beam.

The optical signal component $S_{31}$ represents amplitude of red fluorescence ($\lambda$=680±30 nm) after excitation of the blue laser beam, which corresponds to infrared fluorescence (FL6) emitted from the cell particle dyed with the fluorescent labeling reagent of PE-Cy5. Also, the optical signal component $S_{32}$ represents amplitude of red fluorescence (FL5) emitted from the cell particle dyed with the fluorescent labeling reagent of APC after excitation of the red laser beam.

Further, the optical signal component $S_{41}$ represents amplitude of greenish-yellow fluorescence ($\lambda$=580±30 nm) after excitation of the blue laser beam, which corresponds to greenish-yellow fluorescence (FL2) emitted from the cell particle dyed with the fluorescent labeling reagent of PE. Also, the optical signal component $S_{43}$ represents amplitude of greenish-yellow fluorescence (FL8) emitted from the cell particle dyed with the fluorescent labeling reagent of Ho-Red after excitation of the ultra-violet laser beam.

Furthermore, the optical signal component $S_{51}$ represents amplitude of blue fluorescence ($\lambda$=530±30 nm) after excitation of the blue laser beam, which corresponds to blue fluorescence (FL1) emitted from the cell particle dyed with the fluorescent labeling reagent of FITC. Also, the optical signal component $S_{63}$ represents amplitude of violet fluorescence ($\lambda$=424±44 nm) after excitation of the ultra-violet laser beam, which corresponds to violet fluorescence (FL7) emitted from the cell particle dyed with the fluorescent labeling reagent of Ho-blue.

As described above, according to the present embodiment, the half mirrors HM2-HM6 and the band pass filters BPF2-BPF6 having any selective spectrums are provided between the flow cell 16 and the photomultiplier tubes PMT1-PMT6 so that the photomultiplier tubes PMT1-PMT6 output the pulsed signals for various fluorescence FL1-FL8, each depending upon the spectrums of the optical source and the fluorescent labeling reagent, which are determined as the optical signal components for the fluorescence FL1-FL8. The aforementioned selective spectrums of the half mirrors HM2-HM6 and the band pass filters BPF2-BPF6 are illustrative and exemplary only, the present invention can be adapted to a system having any other selective spectrums. Also, although the isolating circuitry 68 isolates each of the optical signal components $S_{ij}$ in the above embodiment, the logic may be designed to determine the optical signal components $S_{ij}$ only corresponding to the side scattering beam (SSC) and the fluorescence FL1-FL6.

In the meanwhile, the optical signal amplitude detected by the photomultiplier tubes PMT1-PMT6 may vary substantially in accordance with the spectrums of fluorescence, the structure of the half mirrors and the band pass filters, size and features of cell particles, dying condition, etc. Thus, the optical signal components $S_{ij}$ indicated in Table 1 has diversity in scale (detected value) depending on the optical sources 30-34 and the photomultiplier tubes PMT1-PMT6. In order to correct the diversity of the optical signal components $S_{ij}$, the synchronizing circuitry 66 may apply photo-multiplying voltages HV adjustable for each of the photomultiplier tubes PMT1-PMT6, which are synchronized with the first, second and third phases $\delta_1$, $\delta_2$, $\delta_3$ of the optical sources 30-34. For example, the photomultiplier tube PMT2, which detects the optical signal components $S_{21}$ during the phase $\delta_1$ of the first laser beam, is applied with the photo-multiplying voltages $HV_{21}$. Similarly, the synchronizing circuitry 66 may switch the photo-multiplying voltages $HV_{ij}$ (as shown in Table 2) to be applied with each of the photomultiplier tubes PMT1-PMT6, in accordance with respective one of the phases $\delta_1$, $\delta_2$, $\delta_3$ of the optical sources 30-34 so that the scales of the optical signal components $S_{ij}$ are better leveled.

TABLE 2

|  | First Laser | Second Laser | Third Laser |
|---|---|---|---|
| PMT1<br>$\lambda$ = 488 ± 5 nm | $HV_{11}$ | $HV_{12}$ | $HV_{13}$ |
| PMT2<br>$\lambda$ > 749 nm | $HV_{21}$ | $HV_{22}$ | $HV_{23}$ |
| PMT3<br>$\lambda$ = 680 ± 30 nm | $HV_{31}$ | $HV_{32}$ | $HV_{33}$ |
| PMT4<br>$\lambda$ = 580 ± 30 nm | $HV_{41}$ | $HV_{42}$ | $HV_{43}$ |
| PMT5<br>$\lambda$ = 530 ± 30 nm | $HV_{51}$ | $HV_{52}$ | $HV_{53}$ |
| PMT6<br>$\lambda$ = 424 ± 44 nm | $HV_{61}$ | $HV_{62}$ | $HV_{63}$ |

Alternatively, the synchronizing circuitry 66 may switch the amplifying voltages $AMP_{ij}$ (as shown in Table 3) of the amplifying circuitry 70 that electrically amplify the optical pulsed signals output by the photomultiplier tubes PMT1-PMT6, in cooperation with the synchronizing circuitry 66. Thus, the amplifying voltages $AMP_{ij}$ are used for electrically amplifying the optical signal components $S_{ij}$ with more evenly leveled scales.

TABLE 3

|  | First Laser | Second Laser | Third Laser |
|---|---|---|---|
| PMT1<br>$\lambda$ = 488 ± 5 nm | $AMP_{11}$ | $AMP_{12}$ | $AMP_{13}$ |
| PMT2<br>$\lambda$ > 749 nm | $AMP_{21}$ | $AMP_{22}$ | $AMP_{23}$ |
| PMT3<br>$\lambda$ = 680 ± 30 nm | $AMP_{31}$ | $AMP_{32}$ | $AMP_{33}$ |
| PMT4<br>$\lambda$ = 580 ± 30 nm | $AMP_{41}$ | $AMP_{42}$ | $AMP_{43}$ |
| PMT5<br>$\lambda$ = 530 ± 30 nm | $AMP_{51}$ | $AMP_{52}$ | $AMP_{53}$ |
| PMT6<br>$\lambda$ = 424 ± 44 nm | $AMP_{61}$ | $AMP_{62}$ | $AMP_{63}$ |

Since the flow cytometer 1 according to the present embodiment detects the scattering light and the fluorescence for identifying the cell particle 5 that is illuminated with multicolor laser beams, the signal processor 4 preferably detects the optical pulsed signals (optical signal components S) only when the cell particle 5 is moving through the flow cell 16 and illuminated with the laser beams. Otherwise, the signal processor 4 may have to process substantial amount of data including background data irrelevant to the cell particle 5.

The signal processor 4 of the embodiment may constantly monitor the output value V of the pulsed signal, e.g., for the forward scattering beam as described above (FIG. 4), and determine the fact that the cell particle 5 is moving through the focal point within the flow cell 16 only when the output value V exceed a predetermined voltage $V_{th}$ ($V > V_{th}$). Upon determination of the cell particle 5, the signal processor 4 may initiate to retrieve data of the pulsed signals for the side scattering beam and the fluorescence for a predetermined time duration T. Thus, the signal processor 4 uses the output value V of the pulsed signal for the forward scattering beam as a trigger signal to initiate detecting the side scattering beam and the fluorescence.

Although, in the above description, the output value V of the pulsed signal for the forward scattering beam is monitored, the pulsed signal for the side scattering beam or any one of the fluorescence may be monitored for triggering detection of the side scattering beam and the fluorescence. For example, the signal processor 4 may initiate detection of the side scattering beam and the fluorescence upon determining that the output value V of the pulsed signal for the side scattering beam exceeds a predetermined voltage. Alternatively, at least one of the photomultiplier tubes PMT1-PMT6 may be designated as a trigger photomultiplier tube PMT for monitoring the pulsed signal thereof, the signal processor 4 may initiate detection of the side scattering beam and the fluorescence upon determination of the output value V of the trigger photomultiplier tube PMT exceeding a predetermined voltage $V_{th}$.

Figure 6A:
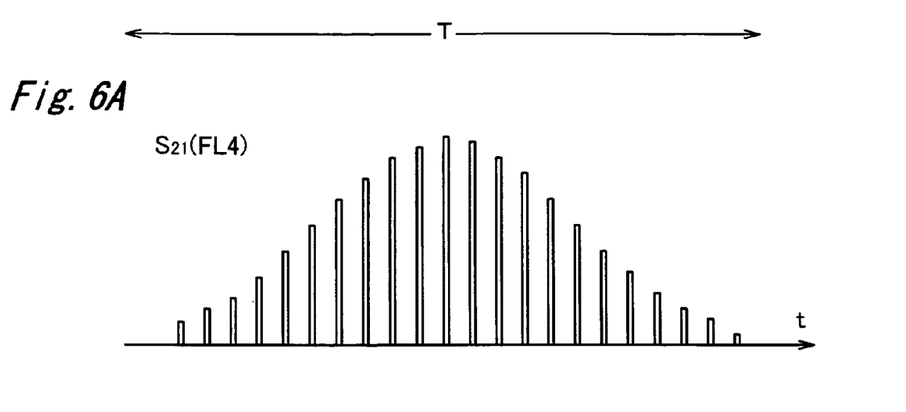
FIGS. 6A-6C are timing charts illustrating transitional changes of the pulsed beam signals output by the photomultiplier tubes.
Figure 6B:
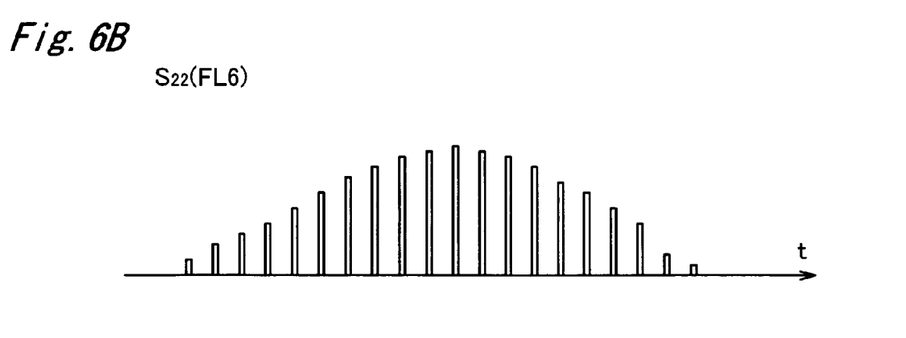
Figure 6C:
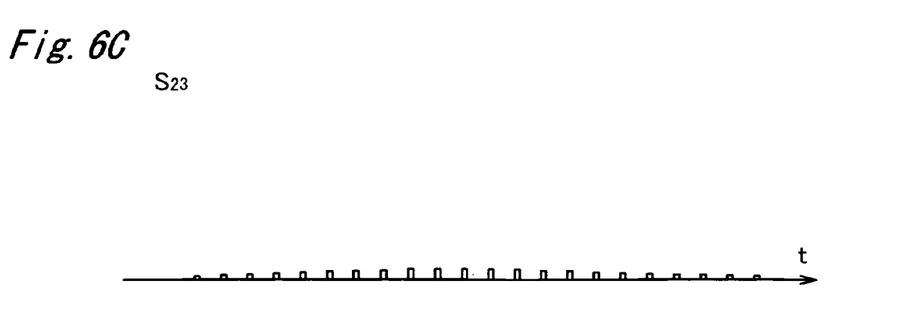

To this result, the signal processor 4 receives from, e.g., the photomultiplier tube PMT2, the optical signal components $S_{21}$(FL4), $S_{22}$(FL6), $S_{23}$, which vary in time as illustrated in FIGS. 6A-6C.

Next, referring to FIG. 5, details and functions of other circuitries composing the signal processor 4 will be described herein. The signal processor 4 includes an analog-digital converting circuitry (A/D converter) 72 for digitalizing each of the optical signal components which are detected by the photodetector PD and the photomultiplier tubes PMT, and then isolated by the synchronizing circuitry 66. Also, the signal processor 4 includes a area/width/height calculating circuitry (A/W/H calculator) 74 for promptly calculating characteristic values that represent area, width, and height of the cell particle 5, directly based upon the optical signal components $S_{ij}$ while such values are conventionally calculated from analog waveform data. A parameter-selecting circuitry 76 selects some of the optical signal components $S_{ij}$ (e.g., FSC, SSC, FL1-FL8) to be processed. A compensating circuitry 78 also uses the digital data of the optical signal components $S_{ij}$ for compensating leakage occurred between fluorescence having different spectrums (fluorescent correction). Then, the selected optical signal components $S_{ij}$ are amplified by a log/linear amplifying circuitry 80 and output to a computer 82 and/or a cell sorter 84.

Upon receiving the digital optical signals for cell particles 5, the computer may be adapted to perform several analysis and evaluation on the cell particles 5 by, for example, providing a chart for a frequency distribution (e.g., dot-plot and histogram) of the cell particles by means of various software applications. Also, the cell sorter 84 may identify the cell particle 5 in response to the optical pulsed signals, thereby to sort the droplets containing particular cell particles 5.

As described above, since a plurality of laser beams are guided to the same optical path according to the present invention, it is possible to detect the forward/side-scattering light and the fluorescence from the cell particles dyed with a plurality of fluorescent labeling reagents, without requiring introduction of the delay time, unlike the conventional flow cytometer and flow cytometry. Also, the present invention substantially facilitates easy adjustment of the optical axes from the optical sources to the flow cell.

The invention claimed is:

1. A flow cytometer, comprising:
    a plurality of optical sources, each of which illuminates an excitation beam at a predetermined frequency having a wavelength and a phase different from another;
    a guide member for guiding the excitation beams into the same incident optical path to focus onto a dyed particle running through a flow cell;
    a plurality of fluorescent detectors for detecting fluorescence from the particle excited by each of the excitation beams to output fluorescent signals; and
    a synchronizing/isolating circuitry for isolating the fluorescent signals in synchronization with each of the phases of the excitation beams into a plurality of optical signal components.

2. The flow cytometer according to claim 1, wherein the fluorescent detector includes a photomultiplier tube, of which photo-multiplying voltage is selectively switched in accordance with respective one of the phases of the optical signal components.

3. The flow cytometer according to claim 1, further comprising an amplifying circuitry for electrically amplifying the fluorescent signals, of which amplifying voltage is selectively switched in accordance with respective one of the phases of the optical signal components.

4. The flow cytometer according to claim 1, further comprising a plurality of band pass filters provided in outgoing optical paths between the flow cell and the fluorescent detectors, for selectively transmitting fluorescence having predetermined spectrums.

5. The flow cytometer according to claim 1, further comprising a forward-scattering beam detector for detecting a forward scattering beam scattered at the particle by each of the excitation beams, to output forward-scattering signals, wherein each of the fluorescent detectors detects the fluorescence for predetermined time duration after the forward-scattering signals exceed a predetermined threshold.

6. The flow cytometer according to claim 1, further comprising a forward-scattering beam detector for detecting a forward scattering beam scattered at the particle by each of the excitation beams, to output forward-scattering signals;
    wherein the fluorescent detectors include at least one trigger fluorescent detector, and wherein the forward-scattering beam detector and each of the fluorescent detectors detect the forward scattering beam and the fluorescence for predetermined time duration after the fluorescent signals detected by the trigger fluorescent detector exceed a predetermined threshold.

7. The flow cytometer according to claim 1, further comprising:
    a forward-scattering beam detector for detecting a forward scattering beam scattered at the particle by each of the excitation beams, to output forward-scattering signals;
    a forward-scattering beam band pass filter provided in outgoing optical path between the flow cell and the forward-scattering beam detector, for selectively transmitting the forward scattering beam having predetermined spectrums;
    a side-scattering-beam detector for detecting a side scattering beam scattered at the particle by each of the excitation beams, to output side-scattering signals; and
    a side-scattering-beam band pass filter provided in outgoing optical path between the flow cell and the side-scattering-beam detector, for selectively transmitting the side scattering beam having predetermined spectrums.

8. The flow cytometer according to claim 1, wherein the optical sources oscillate the excitation beams in a pulsed form at a predetermined frequency having the phase different from another.

9. The flow cytometer according to claim 1, wherein the guide member is configured to reflect the excitation beams such that the reflected excitation beams have the same incident optical path.

10. The flow cytometer according to claim 1, wherein the guide member is configured to direct the excitation beams to the same point of the flow cell.

11. A flow cytometry, comprising:
    illuminating a plurality of excitation beams at a predetermined frequency having a wavelength and a phase different from another;
    guiding the excitation beams into the same incident optical path to focus onto a dyed particle running through a flow cell;
    detecting fluorescence from the particle excited by each of the excitation beams to output fluorescent signals; and
    isolating the fluorescent signals in synchronization with each of the phases of the excitation beams into a plurality of optical signal components.

12. The flow cytometry according to claim 11, wherein said detecting step is performed with a photomultiplier tube, of which photo-multiplying voltage is selectively switched in accordance with respective one of the phases of the excitation beams.

13. The flow cytometry according to claim 11, further comprising:
electrically amplifying the fluorescent signals with an amplifying circuitry, of which amplifying voltage is selectively switched in accordance with respective one of the phases of the excitation beams.

14. The flow cytometry according to claim 11, wherein said detecting of the fluorescence includes selectively detecting the fluorescence having predetermined spectrums.

15. The flow cytometry according to claim 11, further comprising:
detecting a forward scattering beam scattered at the particle by each of the excitation beams, to output forward-scattering signals,
wherein said detecting of the fluorescence is performed for predetermined time duration after the forward-scattering signals exceed a predetermined threshold.

16. The flow cytometry according to claim 11, further comprising:
detecting a forward scattering beam scattered at the particle by each of the excitation beams, to output forward-scattering signals;
wherein said detecting of the fluorescence includes detecting at least one trigger fluorescent detector,
wherein said detecting of the forward scattering beam and said detecting of the fluorescence are performed for predetermined time duration after the fluorescent signals detected by the trigger fluorescent detector exceed a predetermined threshold.

17. The flow cytometry according to claim 11, further comprising:
selectively detecting one of forward scattering beams scattered at the particle by the excitation beams, which has predetermined spectrums, to output forward-scattering signals; and
selectively detecting one of side scattering beams scattered at the particle by the excitation beams, which has predetermined spectrums, to output side scattering signals.

18. The flow cytometry according to claim 11, wherein said illuminating step includes oscillating the excitation beams in a pulsed form at a predetermined frequency having the phase different from another.

19. The flow cytometry according to claim 11, wherein guiding the excitation beams includes reflecting the excitation beams such that the reflected excitation beams have the same incident optical path.

20. The flow cytometry according to claim 11, wherein guiding the excitation beams includes directing the excitation beams to the same point of the flow cell.

* * * * *